(12) United States Patent
Sarvazyan et al.

(10) Patent No.: US 7,922,674 B2
(45) Date of Patent: Apr. 12, 2011

(54) METHOD AND DEVICE FOR REAL TIME MECHANICAL IMAGING OF PROSTATE

(75) Inventors: Armen P. Sarvazyan, Lambertville, NJ (US); Vladimir Egorov, Princeton, NJ (US); Sergiv Kanilo, Lawrenceville, NJ (US); Suren Ayrapetyan, Lambertville, NJ (US)

(73) Assignee: Artann Laboratories Inc, Lambertville, NJ (US)

( * ) Notice: Subject to any disclaimer, the term of this patent is extended or adjusted under 35 U.S.C. 154(b) by 1741 days.

(21) Appl. No.: 11/123,999

(22) Filed: May 6, 2005

(65) Prior Publication Data

US 2009/0005707 A1 Jan. 1, 2009

(51) Int. Cl.
*A61B 5/103* (2006.01)
(52) U.S. Cl. ........................................ 600/587
(58) Field of Classification Search .............. 600/407, 600/437–447, 561, 587, 550; 382/131, 128, 382/209, 217–218, 294–295, 313; 73/172, 73/760, 763
See application file for complete search history.

(56) References Cited

U.S. PATENT DOCUMENTS

| | | | |
|---|---|---|---|
| 5,036,855 A | 8/1991 | Fry | |
| 5,115,808 A * | 5/1992 | Popovic et al. | 600/438 |
| 5,265,612 A * | 11/1993 | Sarvazyan et al. | 600/471 |
| 5,335,669 A | 8/1994 | Tihon | |
| 5,404,881 A | 4/1995 | Cathaud | |
| 5,423,332 A | 6/1995 | Zirps | |
| 5,474,070 A * | 12/1995 | Ophir et al. | 600/437 |
| 5,524,636 A | 6/1996 | Sarvazyan | |
| 5,526,820 A * | 6/1996 | Khoury | 600/561 |
| 5,538,004 A * | 7/1996 | Bamber | 600/443 |
| 5,785,663 A | 7/1998 | Sarvazyan | |
| 5,820,559 A | 10/1998 | Ng | |
| 5,836,894 A | 11/1998 | Sarvazyan | |
| 5,922,018 A * | 7/1999 | Sarvazyan | 600/587 |
| 5,989,199 A * | 11/1999 | Cundari et al. | 600/587 |
| 6,004,267 A | 12/1999 | Tewari | |
| 6,014,473 A * | 1/2000 | Hossack et al. | 382/294 |
| 6,063,031 A * | 5/2000 | Cundari et al. | 600/439 |
| 6,142,959 A * | 11/2000 | Sarvazyan et al. | 600/587 |
| 6,422,997 B1 | 7/2002 | Green | |
| 6,428,479 B1 * | 8/2002 | Aksnes et al. | 600/458 |
| 6,511,427 B1 * | 1/2003 | Sliwa et al. | 600/438 |
| 6,561,980 B1 * | 5/2003 | Gheng et al. | 600/443 |
| 6,569,108 B2 * | 5/2003 | Sarvazyan et al. | 600/587 |
| 6,595,933 B2 * | 7/2003 | Sarvazyan et al. | 600/587 |
| 6,695,787 B2 | 2/2004 | Hogendijk | |
| 6,718,196 B1 | 4/2004 | Mah | |
| 6,760,616 B2 | 7/2004 | Hoey | |
| 6,778,690 B1 * | 8/2004 | Ladak et al. | 382/131 |
| 6,824,516 B2 * | 11/2004 | Batten et al. | 600/439 |
| 2008/0221484 A1 * | 9/2008 | Sarvazyan et al. | 600/587 |

* cited by examiner

*Primary Examiner* — Francis Jaworski
(74) *Attorney, Agent, or Firm* — Boris Leschinsky

(57) ABSTRACT

The present invention relates to a method for real time mechanical imaging of a prostate with a transrectal probe. In the method, generating a composite two- and three-dimensional prostate mechanical image from a plurality of partial mechanical images extracted from pressure response data and a probe orientation data starts with examining the prostate by pressing a probe head pressure sensor array against it at various overlapping locations. Merging of partial mechanical images together is accomplished by analyzing an overlap between each subsequent and previous partial mechanical image. Finding the prostate is assisted with a supplemental pressure response data indicating the location of a sphincter known to be about 4-5 cm away from the prostate. Data processing is improved by including probe orientation data to further increase the accuracy and sensitivity of the method. The probe is equipped with a two-dimensional head pressure sensor array, a supplemental shaft sensor array and orientation tracking sensors including a three-axis magnetic sensor and a two-axis accelerometer sensor for calculating elevation, rotation and azimuth angles of the probe.

7 Claims, 10 Drawing Sheets

METHOD AND DEVICE FOR REAL TIME MECHANICAL IMAGING OF PROSTATE

This invention was made with government support under SBIR Grant 2 R44 CA82620-02A1 awarded by the National Institutes of Health, National Cancer Institute. The government has certain rights in this invention.

BACKGROUND OF THE INVENTION

The present invention relates generally to medical devices. More specifically, it relates to a mechanical imaging system and process for examining, mapping, and diagnosing diseases of a palpable organ such as a prostate gland in a male patient, especially the prostate cancer. It is also applicable more generally to mechanical imaging of palpable tissues, including but not limited to, through natural body openings in a human being, i.e. mouth, ear(s), rectum, and other body cavities. It is also applicable to determination of a relative stiffness or elasticity of tissues. The term "patient" includes humans and animals, both alive and dead that can be subject for mechanical imaging.

The high incidence of prostate cancer, as well as benign prostatic hyperplasia (BPH), especially among the older male population, dictates the need for effective means of early detection. Prostate cancer is the cause of death in about 30,000 men each year, making it the number two cancer killer of men in the United States, second only to lung cancer. However, if prostate cancer is detected early and treated effectively, the chance of survival of one afflicted with this disease improves significantly. Current methods of early diagnosis of prostate cancer include digital rectal examination (DRE), measurement of serum levels of prostate specific antigen (PSA), and transrectal ultrasound (TRUS) examination.

The following discussion provides useful overview of various methods described in the prior art and applicable to prostate examination and imaging.

Substantial prior art is accumulated describing various devices and techniques using ultrasound for the imaging of the prostate. U.S. Pat. No. 6,561,980 by Gheng describes the methods of processing ultrasound images to cause automatic segmentation of prostate, rectum, and urethra once the transverse cross-sectional image of prostate is acquired by ultrasound means. U.S. Pat. No. 6,824,516 by Batten describes a sophisticated system for examining, mapping, diagnosing, and treating prostate diseases based on ultrasonic imaging, this patent is incorporated herein in its entirety by reference. U.S. Pat. No. 6,778,690 by Ladak describes a method of processing 2D and 3D ultrasound images to determine the prostate boundaries and is also incorporated herein by reference in its entirety as it provides useful image processing methodology.

Unfortunately, to date the experience with TRUS as a means of prostate cancer screening and staging has been disappointing. It adds little to screening by DRE and PSA, and the small improvement in prostate cancer detection does not justify its cost. As a screening test, TRUS has a low specificity and a high false positive rate. Evaluation of pathologic specimens shows that a significant fraction of tumors are isoechoic and thus indistinguishable from surrounding tissue, while many palpable tumors could not be visualized by TRUS.

The most sensitive single test for prostate cancer is measurement of serum PSA levels. However, its positive predictive value is limited. The DRE alone is even less useful. However, combining the two modalities nearly doubles the cancer detection rate. Large-scale studies of systematic screening for prostate cancer using PSA, DRE and TRUS concluded that combining PSA and DRE provided the highest sensitivity and specificity for prostate cancer diagnosis. Therefore, the combination of the two methods for prostate cancer screening is currently recommended by the AUA and American Cancer Society, and has been approved by FDA for patients between the ages of 50 and 75 years.

At the present time, digital rectal examination is the most widely used method of prostate cancer screening. Approximately 30-50% of palpable prostate nodules prove to be malignant upon pathologic evaluation. Screening trials have demonstrated that 70% of men with abnormal DRE undergoing radical prostatectomy have organ-confined cancer. A strong association between abnormal DRE and prostate cancer mortality has been demonstrated and it was suggested that screening DRE could prevent as many as 50-70% of deaths due to prostate cancer. DRE also has been shown to be the most cost efficient prostate screening method, especially when combined with PSA.

The main disadvantage of DRE is its high degree of subjectivity. The user has to instinctively relate what he or she senses by the finger to previous DRE experience. There may not be a sufficient number of skilled users available for large-scale mass prostate screenings. Another limitation of DRE is that a physician performing the examination cannot objectively record the state of the examined prostate. Therefore, it is difficult to objectively compare the results of consecutive examinations of the same prostate.

A new method of prostate imaging based on principles similar to those of manual palpation has been developed by Sarvazyan et al. and described in the U.S. Pat. Nos. 6,569,108; 6,142,959; 5,922,018; 5,836,894; 5,785,663; and 5,524,636, all incorporated herein in their entirety by reference. This method, termed Mechanical Imaging, provides the ability to "capture the sense of touch" and store it permanently for later temporal correlation and trending. The essence of mechanical imaging is measurement of the stress pattern on the surface of the compressed tissue and analyzing the changes of that pattern while moving the sensor array over the examined tissue. Temporal and spatial changes in the stress pattern provide information on the mechanical structure of the examined tissue and enable 3D reconstruction of internal structures and mechanical heterogeneities in the tissue. Mechanical imaging is free of many of the disadvantages of DRE. Mechanical imaging has been shown to exceed substantially the limits of lesion size and depth detectable by conventional manual palpation techniques [Weiss R., Hartanto V, Perrotti M, Cummings K, Bykanov A, Egorov V, Sobolevsky S. "In vitro trial of the pilot prototype of the prostate mechanical imaging system", Urology, V.58, No. 6, 2001, p. 1059-1063].

Recently, the American Urological Association issued recommendations to help physicians confirm the diagnosis of prostate cancer. According to these recommendations, a biopsy should be considered for any patient with an abnormal DRE and elevated PSA. The effectiveness and reliability of DRE are highly dependent on the skill of the user, since the finger does not provide a quantitative or objectively verifiable assessment. Thus, there is a great need for a new technology and a device to enable general practitioners and urologists alike to perform a reliable, accurate, sensitive, and quantitative assessment of the prostate using a computerized palpation-imaging device. Moreover, such accurate assessment of prostate size, shape, and elasticity is also important for diagnosing and monitoring of prostate cancer and BPH. Mechanical imaging technology and the low cost, prostate imaging device should improve significantly the ability of minimally trained individuals in primary care settings to assess, screen, and monitor prostate pathology in a reliable and valid manner in a male human, with a minimum of physical and mental discomfort.

While prior art mechanical imaging devices provided for data collection, the ability to recreate the 2D and 3D images of the prostate were limited by the insufficiently accurate information about the position of transrectal probe with regard to the examined prostate in the course of examination. One reason for this is because the prostate can shift from its original place during the procedure. Therefore, the prior art methods have a fundamental disadvantage in that as the examination progresses, no means are available to properly compensate for the probe position and orientation relative to the moving prostate. Inaccuracies in the evaluation of the location of the prostate with respect to the probe head during the course of examination may result in low quality of obtained images and introduce various artifacts.

The need exists therefore for a prostate examination means and methods of use designed to eliminate the distortion in the position data of the prostate probe and make it independent of the internal movements of the prostate organ.

SUMMARY OF THE INVENTION

Accordingly, it is an object of the present invention to overcome these and other drawbacks of the prior art by providing a novel method and device for mechanical imaging of a palpable organ such as a prostate gland through a natural body opening, this method and device having the ability to generate real time 2D and 3D depiction of the organ and automatic detection of suspicious areas within thereof.

It is another object of the present invention to provide a mechanical imaging device for examination of prostate capable of automatically compensating for the internal shifts of the prostate during the examination.

It is another object of the present invention to provide a mechanical imaging device for examination of prostate capable of merging at least two independently obtained mechanical images of prostate using commonly identified features of the prostate image from an overlap between these two images.

It is a further object of the present invention to provide a probe for prostate examination equipped with a two-dimensional pressure array sensor capable of providing mechanical images with the ability to recognize the overlap between these two images.

The method of the invention is based on a method for real time mechanical imaging of the palpable organ with a probe inserted through a natural body opening. According to one aspect of the method of the invention, generating a two- or three-dimensional prostate mechanical image from a plurality of pressure response data and probe orientation data comprises the steps of:

locating the prostate under the transrectal probe head pressure sensor array, examining the prostate by the probe head two-dimensional sensor array by pressing it repeatedly against the prostate at various locations such that each subsequent location overlaps the previous location, incorporating newly acquired mechanical prostate information from each location where the probe is pressed against the prostate into a partial two-dimensional normalized mechanical image of the prostate, comparing each subsequent partial mechanical image with the previous partial mechanical image to find an overlap therebetween, and constructing a composite mechanical image of the prostate from the entire plurality of partial mechanical images using overlaps between each subsequent and previous partial mechanical image to merge them together.

Importantly, the processing of data obtained from the probe head pressure sensor array allows moving the probe relative to the prostate while maintaining the common identified features of each obtained partial mechanical image. In other words, every time the probe is moved from one location to the next, the processing means of the device are adapted to follow certain identifiable features from the overlap between the previous partial mechanical image to the next one such that a complete 2D or 3D image may be constructed. That way, there is less or even no need for knowing the absolute position in space of both the prostate and the probe in order to accurately relate each successive mechanical image to a certain part of the prostate.

In the preferred embodiment, the device comprises: a probe shaft pressure sensor array for collecting pressure response data in the vicinity of the sphincter; a probe head pressure sensor array for collecting data in the vicinity of the prostate volume; a probe orientation tracking sensors for collecting a probe orientation data; a processing apparatus for processing the pressure response and orientation data to generate mechanical image data and calculate prostate parameters; and a display device for representation of at least a two-dimensional image of the prostate.

Preferably, in order to further increase the accuracy of the results, the probe head orientation and its position relative to examined prostate is calculated from orientation data recorded from 3D magnetic sensors and a 2D accelerometer sensor, and combined with the pressure response data recorded from the head pressure sensor array and the shaft pressure sensor array.

As opposed to the devices of the prior art, the present invention takes advantage of combining three independent sources of positioning information:

using the prostate itself as a reference object by examining the overlap between each previous and subsequent partial mechanical image of the prostate, having more than one pressure sensor arrays working together in an integrated manner to take advantage of locating the prostate in its relationship to a nearby organ, which is more stable in its position such as sphincter, and finally calculating of probe head position from probe orientation data.

Combining all these sources of information, the device of the invention provides calculations including both the orientation and pressure response data.

The device and method of the present invention are created with a design philosophy to create a patient-friendly system, which is easy and intuitive to use by the examining physician.

As a result, the present invention advantageously provides for:

early prostate cancer detection;

quantitative classification of prostate geometrical and mechanical parameters;

automatic identification of what has changed between successive examinations;

tracking and trending treatment impact for certain treatment modalities;

matching the system output with pathology findings as proof of system performance.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION OF THE PREFERRED EMBODIMENTS OF THE INVENTION

A detailed description of the present invention follows with reference to accompanying drawings in which like elements are indicated by like reference letters and numerals.

Figure 1:
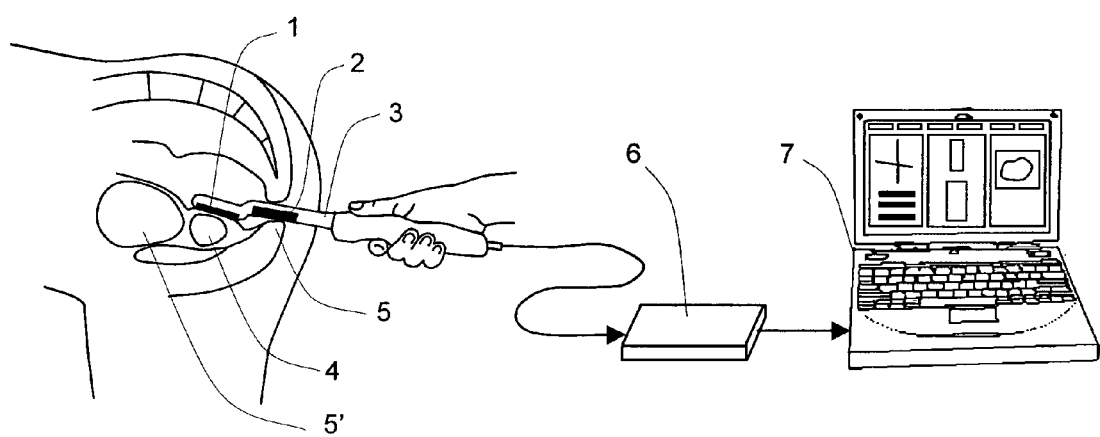
FIG. 1 is a schematic diagram illustrating the functional structure of the system in accordance with the present invention.

Referring now to the drawings, FIG. 1 is a schematic view of a preferred embodiment of a device for generating a mechanical image of a three-dimensional prostate volume from pressure response data corresponding to a scan of the prostate. The device comprises the following major elements:

a transrectal probe 3 with incorporated two-dimensional head pressure sensor array 1 for receiving pressure response data for the prostate 4 and shaft pressure sensor array 2 for receiving supplemental pressure response data for a sphincter area 5, electronic unit 6, and a processing and displaying means 7, which may be for example incorporated into a compact personal computer.

The prostate examination is performed using the following general steps. The patient is instructed to take off all clothes below the waist. The examination is preferably performed in the standing position by bending the patient over the examination table to form a 90-degree angle at the waist. Patient' chest is placed on the table and patient's weight is applied to the table surface so that leg muscles are free from any tension. Optionally, the patient can also be examined while positioned on his side, with his knees bent toward his chest. The probe is preferably covered with a disposable lubricated cover. During the insertion into the rectum, pressure applied to the anal sphincter should be monitored in order to minimize the level of patient' discomfort. Pressure response data obtained from a supplemental pressure array may be optionally used for that purpose. Gentle posterior pressure is applied as the probe is slowly inserted with the sensor surface down. Allowing a few seconds for the external and internal sphincter to relax will avoid patient discomfort. Scanning begins in the sagitall plane by first optionally imaging the sphincter used as a supplemental reference organ. Then, the probe is inserted deeper until the bladder is visualized. Next, by sliding the probe backwards, the prostate is detected at about 4-5 cm from the sphincter and the probe is positioned in a way that enables the device to display the prostate gland surface in the center of the screen. Once the probe is properly positioned, evaluation of prostate is performed through a set of multiple pressings on the median sulcus and lateral lobes of the prostate. Each location of compression of the prostate is done such that it overlaps the previous location of such compression. In certain cases, change in an elevation angle of the probe is required to visualize the prostate.

Figure 2:
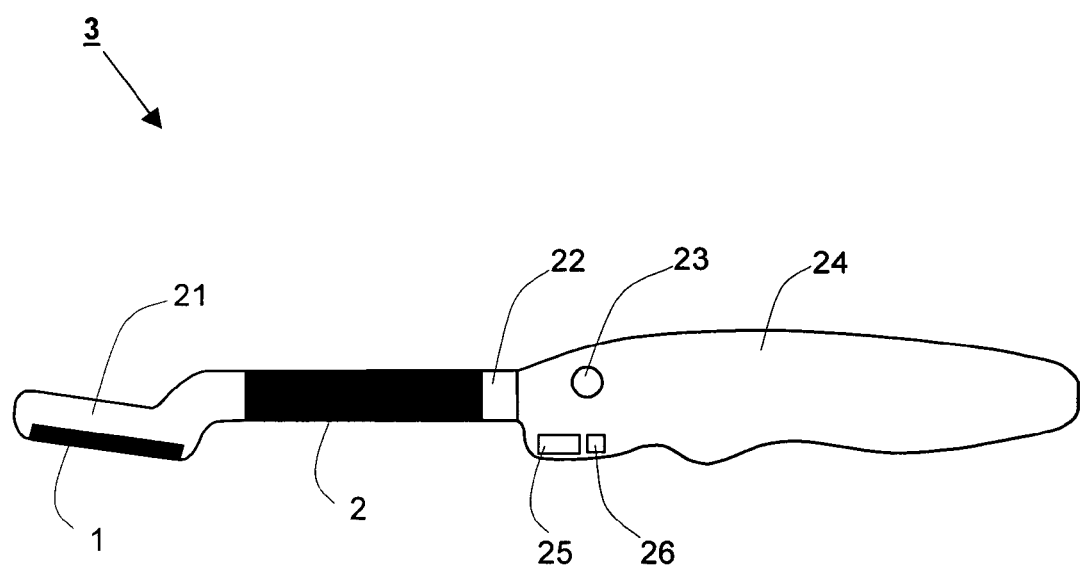
FIG. 2 is a side view of the probe with a two-dimensional head pressure sensor array, a shaft pressure sensor array, and orientation sensors.

FIG. 2 is a side view of the preferred embodiment of the transrectal probe 3 with the head pressure sensor array 1 installed on a probe head 21, and with the shaft pressure sensor array 2 installed on a probe shaft 22 attached to the probe handle 24. The optional elastic disposable cover (not shown) is envisioned to envelop the entire surface of the probe head 21, probe shaft 22, and partly the probe handle 24. The probe handle 24 further comprises orientation tracking means consisting of a three-axis magnetic sensor 25 and a two-axis accelerometer sensor 26. The probe also includes an examination "start-stop" button 23. Of note here is the offset of the probe head 21 relative to the probe shaft 22. It is designed such that the probe better fits with the anatomy of a human patient, so that compression of the prostate does not cause loading the sphincter with a side force. Both the shaft and the head pressure sensor arrays are better adapted to visualize the prostate and the sphincter respectively.

Figure 3A:
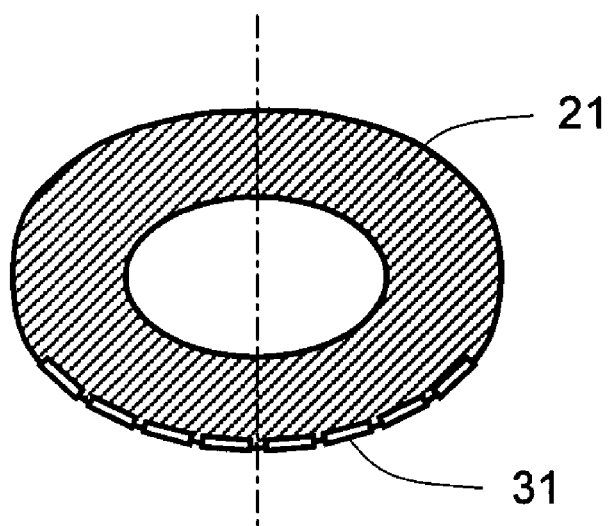
FIGS. 3A and 3B are cross-sectional views of the probe head and the probe shaft respectively in accordance with the present invention.

FIG. 3A is a preferred cross-sectional view of the oblong probe head 21 with surface installed pressure sensors 31 in accordance with the present invention. The probe of the invention is equipped with a two-dimensional pressure sensor array with over 60 individual sensors arranged in a two-dimensional array, for example 8×16 or 16×16. Importantly, the number of sensors, their density, and array configuration is selected to provide sufficient pressure response data to obtain two-dimensional pressure data in each pressing of the probe against the palpable organ. When each subsequent location in which the probe is pressed against the prostate overlaps the previous location, resolution of the pressure array should be sufficient to identify such overlap between the partial mechanical images corresponding to a previous and subsequent location, as discussed in more detail below. Previously known devices of this type were not capable of obtaining a two-dimensional pressure patterns after a single pressing since they were equipped with just a linear array of sensors or had limited number of sensors. That was insufficient for obtaining useful two-dimensional patterns by making just a single pressing of the pressure sensing array. A plurality of pressure sensors 32 constitutes the pressure sensing array of the head pressure sensor array 1 as shown in FIG. 2. The two-dimensional pressure sensor array 1 serves the following three main purposes:

providing pressure response data in the course of examination of the prostate, providing information on changes in the probe head position relative to the prostate deploying a mechanical image recognition technique, and guiding the user during prostate examination by displaying a real time complete two-dimensional pressure pattern of the head pressure sensor array.

Size, grid, and sensor quantity in the head pressure sensor array may very. Preferably, the head pressure sensor array has a pressure sensitive area of about 12 to 20 mm wide by 30 to 50 mm long, and includes over 60 individual pressure sensors. The curvature radius of the probe head may vary too, but preferably the curvature radius should be about 10 to 20 mm to provide a uniform stress pattern while pressing against the prostate. Individual pressure sensors may be designed to be a piezoelectric, resistive, or MEMS pressure transducer, possibly using micro-machined parts or nano-technologies. Preferably though, each pressure sensor comprises a capacitive pressure transducer covered by an elastic compound.

Figure 3B:
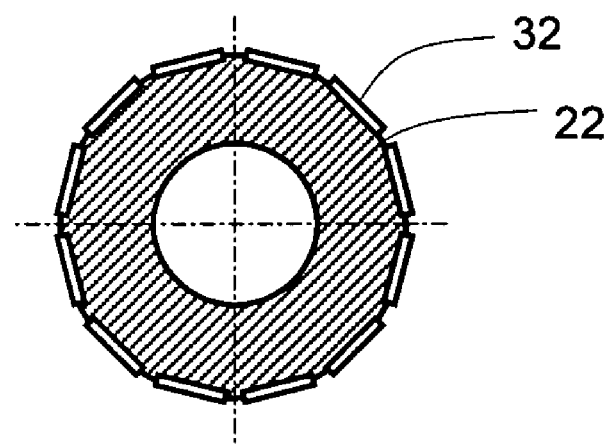

FIG. 3B is a preferred cross-sectional view of the probe shaft 22 with surface installed supplemental pressure sensors 32 in accordance with the present invention. A plurality of supplemental pressure sensors 32 constitutes the shaft pressure sensor array 2 as shown in FIG. 2. This shaft pressure sensor array serves two main purposes:

receiving supplemental pressure data from the sphincter area needed to guide the user during prostate examination by displaying a real time complete two-dimensional pressure pattern of the shaft pressure sensor array, and assisting the user in estimating a most probable location of the prostate being typically at a distance of about 4-5 cm away from the location of the sphincter.

As with the head pressure sensor, the size, grid, design, and sensor quantity in the supplemental shaft pressure sensor array may very. In the most basic case, it can be a simple linear array of sensors. Preferably, the shaft pressure sensor array has a pressure sensitive area all the way around the probe shaft sized to be about 40 mm long and include over 600 individual pressure sensors. A shaft diameter may vary too, but preferably the shaft diameter is about 12.5 mm. Each individual pressure sensor may be a piezoelectric, resistive, or MEMS pressure transducer, but in the preferred embodiment it is a capacitive transducer, similar to that of the head pressure sensor array.

Figure 4:
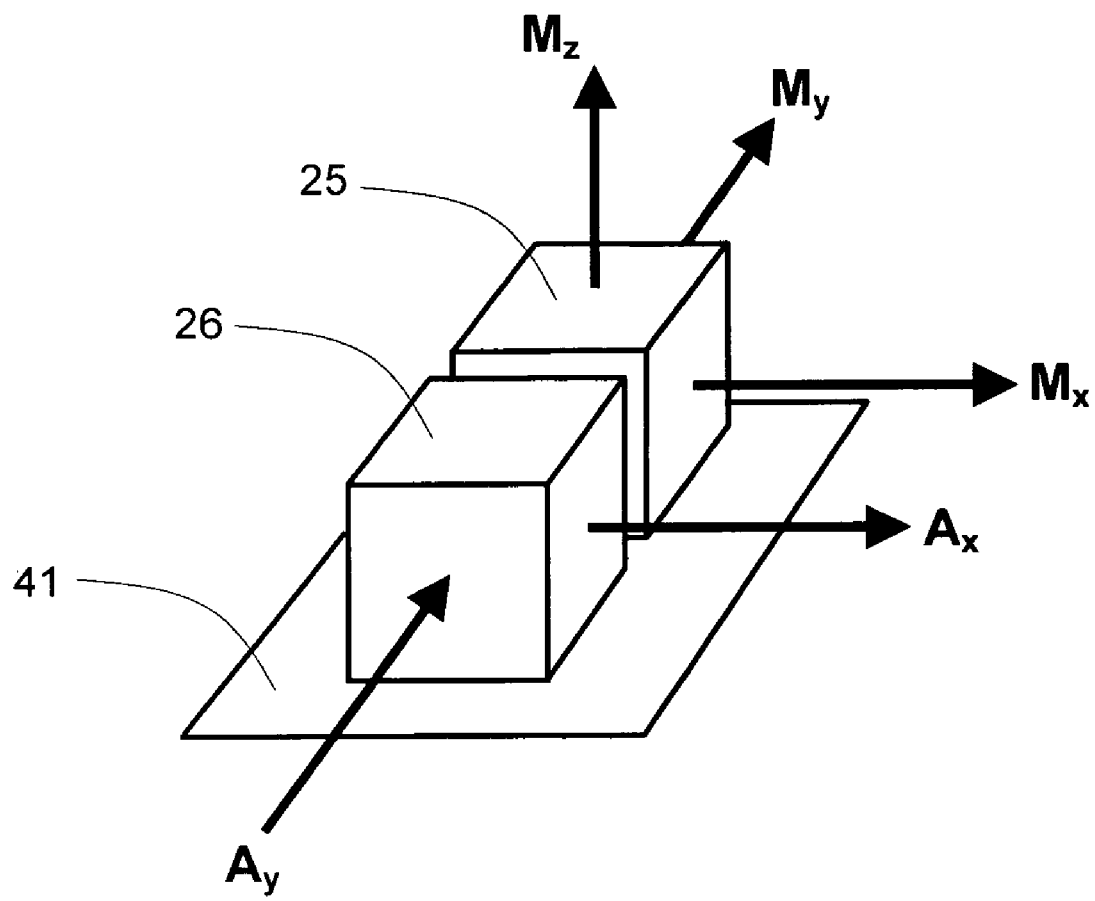
FIG. 4 is a diagram of an orientation tracking system used in the preferred embodiment of the present invention.

FIG. 4 is a diagram of an orientation tracking sensor means used in the preferred embodiment of the present invention. The orientation tracking means includes a three-axis magnetic sensor 25 with orthogonal sensitivity axes $M_x$, $M_y$, $M_z$, and a two-axis acceleration sensor 26 having sensitivity axes $A_x$, $A_y$ accordingly. Importantly, $A_x$-axis is parallel to the $M_x$-axis and $A_y$-axis is parallel to the $M_y$-axis. Both the magnetic sensor 25 and the acceleration sensor 26 are mounted on a platform 41 so that X and Y axes are parallel thereto, which in turn is parallel to the probe head pressure sensing surface. Preferably, platform 41 is incorporated inside the probe handle to be in the vicinity of the sphincter during prostate examination. Magnetic sensor readings give sensor orientation relative to Earth's magnetic field. To compensate the magnetic sensor reading for a platform tilt relative to a horizontal plane, which is perpendicular to Earth's gravity vector, it is necessary to know the platform tilt angles. The two-dimensional accelerometer sensor is used here as a tilt sensor to provide elevation ($\phi$) and rotation ($\theta$) readings. The X, Y, Z magnetic readings can be traced back to the horizontal plane by applying the rotational equations shown below:

$$Xh = X*\cos(\phi) + Y*\sin(\theta)*\sin(\phi) - Z*\cos(\theta)*\sin(\phi) \quad (1)$$

$$Yh = Y*\cos(\theta) + Z*\sin(\theta) \quad (2)$$

where Xh and Yh are Earth's magnetic vector projections to the horizontal plane. Once Xh and Yh are known, it is possible to calculate an azimuth angle as:

$$\text{azimuth} = \text{arc Tan}(Yh/Xh)$$

To facilitate the use of the accelerometer sensor as a tilt sensor, a known low-pass filter may be applied.

In use, upon pressing the "start" button on the probe handle, the processing means 7 is supplied with all angle readings and calculates current azimuth angle to set this azimuth angle as a azimuth reference angle equaling to zero. At the same time, an orientation closeness of azimuth angle discontinuity to this azimuth reference angle is calculated. In case this closeness exceeds a predetermined threshold, axes X and Y are mutually changed in equations (1), (2) to move away the azimuth angle discontinuity from a probe operation range. All azimuth angles thereafter and during prostate examination procedure are calculated relative to that azimuth reference angle so that the user may observe in real time all probe orientation angles: azimuth, elevation, and rotation.

Figure 5:
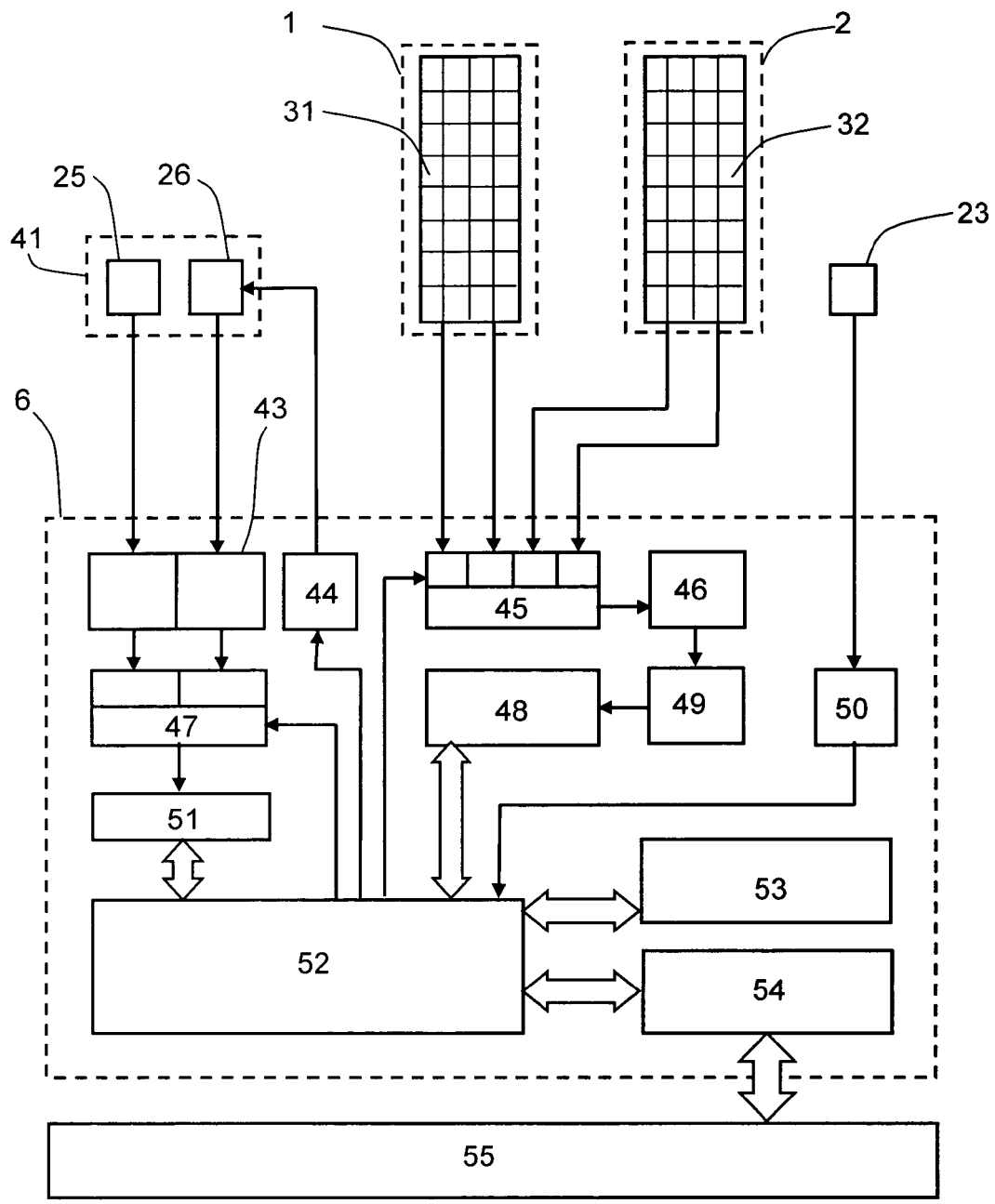
FIG. 5 represents an electronic unit schematic diagram of the device.

FIG. 5 represents a schematic diagram of an electronic unit 6 of the device in accordance with the present invention. A plurality of pressure sensors 31 forming the head pressure sensor array 1, and a plurality of pressure sensors 32 forming the shaft pressure sensor array 3 are shown on the diagram. A pressure sensing circuit inside the electronic unit 6 comprises an analog switching unit 45, amplifier 46, converter and/or integrator 49, designed to amplify and convert respective electrical signals generated by each pressure sensor for detecting a pressure imposed on each sensor during prostate examination. Analog-to-digital converter 48 transforms analog input signal into a digital signal and sends it to a processor 52. A plurality of amplifiers 43 amplify signals generated by accelerometer sensor 25 and magnetic sensor 26 described above for detecting the probe orientation during pressing against the prostate and movement of the probe from one pressing site to another. The amplified signals from amplifiers 43 are sent to multiplexer 47. Multiplexed signals are converted to digital signals by analog-to-digital converter 51 and sent to processor 52. A set/reset circuit 44 controlled by the processor 52 generates set/reset pulses supplied to magnetic sensor 26 to optimize the magnetic domains for most sensitive performance. Structure and functional characteristics of set/reset circuit 44 are determined by the type of magnetic sensor used for the design of the probe and by recommendations of specific magnetic sensor manufacturer. A control button 23 mounted on the transrectal probe handle is connected to the processor 52 through a driver 50 for controlling the prostate examination process and providing at least a stop/start function. Processor 52 communicates with analog-to-digital converters 48 and 51, multiplexers 45 and 47, and a communication port 54 to support data exchange with external processing and displaying means 55. Preferably, the external processing and displaying means 55 is a compact laptop computer. Data storage unit 53 may be used in electronic unit 6 for storing prostate examination data and intermediate information needed for proper functioning thereof, for example orientation sensor calibration data, pressure sensor calibration and tuning data, etc. The processing means is designed to automatically detect pressure sensors malfunction such as for example excessive noise and impaired sensitivity and excludes any defect sensor data from acquired pressure data frames.

The external processing and displaying means 55 is intended to serve for examination data processing. It is adapted to perform the following functions:

calculate the position of each pressure sensor during prostate examination,
approximate and correct partial mechanical images of the prostate and surrounding tissues,
separate and analyze the prostate partial mechanical images,
determine the prostate geometrical parameters and mechanical parameters of prostate inner structures such as lesions, nodules, stiffer tissue and the like, and
prepare the prostate images for visualization, as described below.

The displaying means 55 preferably has a touch screen functions to communicate with the device during prostate examination.

Figure 6:
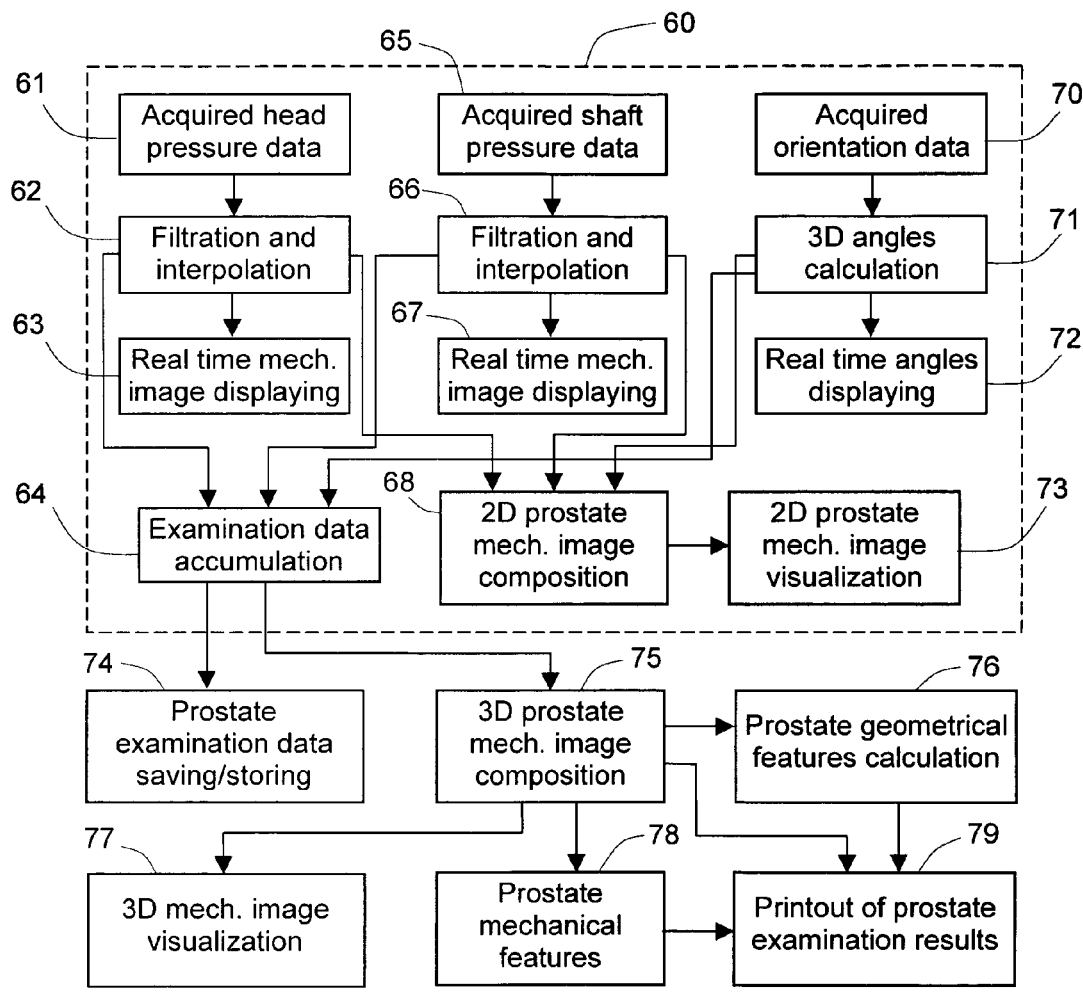
FIG. 6 is a flow chart describing steps for obtaining diagnostic information.

FIG. 6 is a flow chart describing steps for obtaining diagnostic information in accordance with the present invention. Head pressure signal is first acquired from the probe head pressure sensor array and then transformed into head pressure response data 61 expressed for example in kPa according with the sensor calibration characteristics. After temporal and two-dimensional spatial filtering in block 62, the data is displayed for the user (in block 63) in real time during prostate examination. It allows the user to guide the probe helping in detection of any abnormal or suspicious sites in the examined prostate. Shaft pressure signal is acquired from the probe shaft pressure sensor array and transformed into a shaft pressure response data 65 expressed for example in kPa according to the sensor calibration characteristics. After a temporal and two-dimensional spatial filtering in block 66, it is also displayed (block 67) in real time during prostate examination. This allows visualizing a part of sphincter area to guide the user in finding prostate and assisting in the probe navigation. Orientation data 70 is acquired from the probe orientation sensors. Further, after calculation of azimuth, elevation and rotation angles in block 71, these angles are displayed (block 72) in real time during the prostate examination to guide the user in probe navigation.

After locating the prostate under the probe head pressure sensor array, the user presses the examination start/stop button on the probe handle to start a real time prostate mechanical image composition algorithm (block 68). Description of this algorithm is given below in explanations of FIG. 9. The two-dimensional prostate mechanical image is composed and displayed in block 73. Simultaneously, the prostate examination data including that pressure response and probe orientation data are accumulated in block 64. All operations in block 60 take place in real time during prostate examination.

After completing the prostate examination, the user presses again the examination start/stop button on the probe handle to stop the real time prostate mechanical image composition algorithm, and to go to examination data saving procedure in block 74. A three-dimensional prostate mechanical image composition algorithm in block 75 is running automatically as described in detail below. The composed three-dimensional mechanical prostate image may be visualized in block 77. Prostate geometrical parameters and mechanical parameters are calculated in blocks 76 and 78 respectively. Printout of the prostate examination results (block 79) includes a series of prostate mechanical images representing the most distinctive prostate findings and quantitative prostate data such as a size, symmetry, medium groove, lesion detection classifier outputs and alike.

Figure 7:
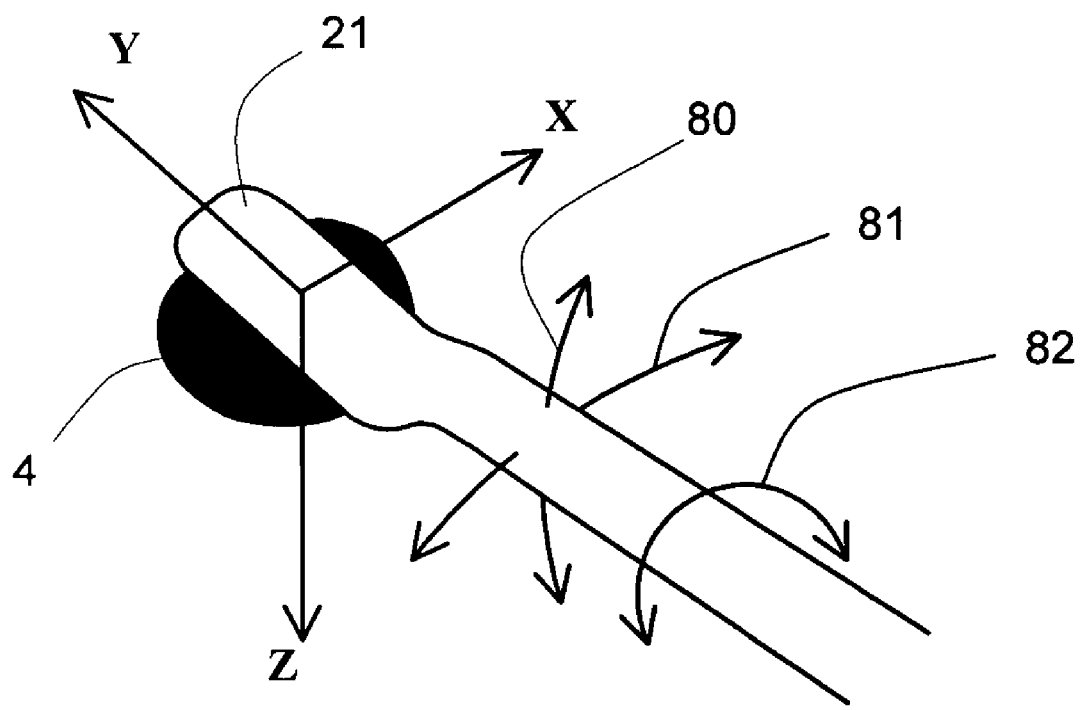
FIG. 7 is a perspective view of the transrectal probe relative to an examined prostate, illustrating a reference coordinate system having three orthogonal axes and probe orientation angles.

FIG. 7 is a perspective view of a probe relative to an examined prostate illustrating a reference coordinate system having three orthogonal axes and probe orientation angles. A processing means defines the reference coordinate system X, Y, Z at the moment of first capturing a prostate mechanical image when a total pressure prostate signal exceeds a predetermined threshold after pressing the start examination button on the probe handle. The following instant orientation angles are defined as reference angles for the reference coordinate system X, Y, Z: elevation (80), azimuth (81), and rotation (82). All subsequent probe orientation angles relative to the reference system X, Y, Z are calculated relative to these reference angles. The probe head 21 is pressed against the prostate 4, when the first capturing a prostate mechanical image occurs. In a preferred method of the invention, a probe rotation angle should be maintained close to zero. Despite of the presence of the probe head pressure sensing surface curvature, the mechanical image projection along X-coordinate on X, Y-plane is done without taking into account that curvature. The probe head mechanical image is acquired as a 2D image and used for prostate image reconstruction inside a defined three-dimensional prostate volume. For the simplicity of real time calculations, the two axes X and Y of the reference coordinate system X, Y, Z are positioned in the mechanical image plane of the probe head pressure sensor array, while the third reference or Z-coordinate is perpendicular to the mechanical image plane.

Figure 8:
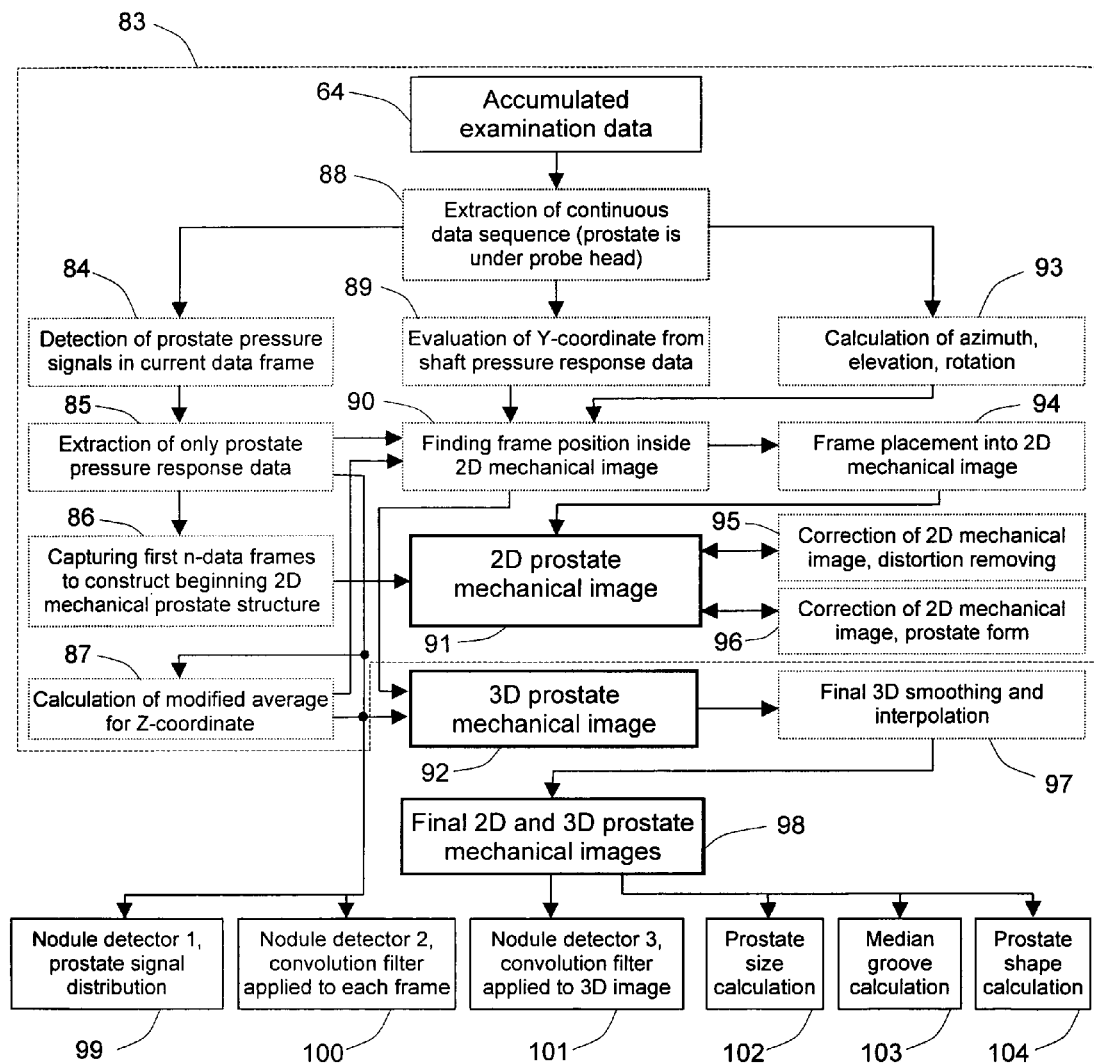
FIG. 8 is a flow chart describing steps for composition of two-dimensional and three-dimensional prostate mechanical images and calculating prostate parameters.

FIG. 8 is a flow chart describing the steps necessary for composition of a two-dimensional and a three-dimensional prostate mechanical image and calculating prostate parameters. These algorithms can be activated in real time during prostate examination as marked by dashed line 83 or after the examination is complete when all examination records are available (block 64). The first step includes extraction of continuous pressure data sequence from the head pressure sensor array by means for calculating a plurality of partial mechanical images of the prostate. One partial mechanical image is calculated each time when the prostate is located under the probe head, so that this data will be used later in prostate image composition. The purpose of this extraction is to exclude sphincter signals from the head pressure data during the probe insertion into the rectum.

Detection of prostate partial mechanical image in pressure response data recorded from the head pressure sensor array is done in block 84 by using an algorithm, which estimates the probability that mechanical image has a pressure signal increase in its central part. The possibility that some sensors could produce an erroneous signal, as well as that some rows and column in the sensor array could have incorrect tuning or calibrating are taken into account. Such column and row errors may cause false pressure jumps or gaps in the pressure data. For each interior row or column of the sensor array, the detection algorithm calculates a pressure signal value relative to the linear interpolation based on the boundary pressure. A predetermined number of points with highest and lowest pressure values are discarded. The positive or negative sign of the sum of remaining values defines the sign of the entire line. Each line (row or column) is assigned a certain weight, the highest for the central lines, and the lowest for boundary lines. If the sum of the weights for all lines with corresponding signs is greater than a predefined value, it is considered that the mechanical image contains the prostate imprint. The sum is then normalized to a predetermined range, using two scale parameters, which gives a quantitative estimation of the presence of a prostate imprint in the mechanical image. If no prostate pressure signal was detected inside the analyzed pressure data frame, this data frame is discarded. On the opposite, if the prostate pressure signal was detected, the next procedure in block 85 activates extraction of only the prostate pressure response data (pixels) inside analyzed pressure response data frame.

The procedure for isolation of a partial prostate image consists of separation of one or several relatively big coherent zones containing a relatively high pressure signal. Another purpose of this procedure is to reduce the influence of boundary effects and suppression of pressure peaks in the top and bottom parts of the sensor array corresponding to the sphincter and bladder pressure signals. This procedure starts with quadrupling the number of pixels in the image using two by two interpolations between neighboring sensors. The binary image of the pressure pattern is created by setting all pixels for which the pressure is higher than average to black. At the same time, the pixels for which the pressure is lower than average are set to white. Two types of filtering are applied thereafter to the binary image. The expanding filtering calculates the number of black pixels adjacent to each white point. If the number is higher than the predetermined value, it turns the white point into a black point in order to enlarge the black regions and cover small white holes. The squeezing filtering is applied next to achieve the same but opposite effect for black points. It calculates the number of white pixels adjacent to each black point. If that number is higher than the predetermined value, it turns it to the white point in order to squeeze black zones and smooth their edges. A sequence of expanding and squeezing removes or significantly reduces small boundary defects, eliminates the inner white holes, combines and rounds large inside zones. The resulting black zone is mapped back to the pressure sensor array, and only the pressure sensors, which belong to the black zone, are allowed to participate in the next phase of prostate image analysis.

Important advantage of the present invention is its ability to use the prostate itself as a reference object. After determination of prostate partial images earlier in the sequence, this is accomplished in the next few steps by the means 86 for constructing of the composite prostate image. Specifically, in the block 86 the first n-frames of pressure response data are captured to construct a first pass two-dimensional mechanical prostate structure. This capture is occurring when the total pressure prostate signal exceeds a predetermined threshold. After averaging, the captured first pass prostate structure is transferred into a two-dimensional composite prostate image 91. After that, each subsequent pressure response data carrying the prostate partial mechanical image is analyzed in means for comparing partial mechanical images 90 to find an overlap area with the previous partial mechanical image. Subsequently, means for constructing the composite image 94 are used for placing new partial mechanical image into the composite two-dimensional prostate mechanical image. Block 90 runs a matching algorithm trying to find best fit of a current prostate partial mechanical image inside the two-dimensional composite prostate mechanical image. Preferably, the best fit is calculated by maximizing a functional F $$F(n, m) = \sum_{i,j=0}^{i=k,j=l} S_{i,j} * P_{n+i,m+j} \tag{4}$$

for $n \subset (-k/4, +k/4),$ $m \subset (-l/4, +l/4)$ where k and l are quantities of horizontal and vertical pixels inside the pressure frame with the current prostate mechanical image, n and m are maximum possible image shift in pixels relative to a previous fitted mechanical image, $S_{i,j}$ is current pressure response signal of i,j pixels, and $P_{n+i,m+j}$ is a pressure signal of n+i ,m+j pixel inside the two-dimensional composite prostate image.

After the best fit is found, each pixel of a current partial mechanical prostate image is placed into the two-dimensional composite prostate image with a predetermined weighted factor if its current value exceeds respective pixel value inside the two-dimensional composite prostate image (block 94). Preferably, all calculations in blocks 86, 90, 91, and 94 are implemented with normalized pixels, so that each pixel value of the prostate mechanical image is divided by a modified average of analyzed pressure data frame calculated inside block 87. The modified average $\overline{S}$ is calculated according to equation (5) after removing a predetermined quantity (b) of pressure pixels $S^{max}$ having maximum values.

$$\overline{S} = \left( \sum_{i,j=0}^{i=k,j=l} S_{i,j} - \sum_{q=0}^{q=b} S_q^{max} \right) \Big/ (k*l-b) \tag{5}$$

where k and l are quantities of horizontal and vertical pixels inside the pressure response frame with the analyzed prostate mechanical image, $S_{i,j}$ is an instant pressure signal of i,j pixels.

Azimuth, elevation, and rotation angles calculated for the instant pressure response data frame in block 93, and evaluated Y-coordinate from shaft pressure data in block 89 are used in finding a frame local reference position inside the two-dimensional mechanical image space to start matching algorithm in the accordance with equation (4). Simultaneously, a procedure 95 of removing image distortion and procedure 96 of correction of the two-dimensional mechanical image 91 are run during prostate examination. The procedure 95 smoothes any distortions above a predetermined threshold in the calculated a two-dimensional gradient field inside the image 91. Procedure 96 corrects a prostate form if prostate form distortion exceeds the bounds of an acceptable prostate form variety.

Each pressure response data carrying a partial mechanical image of a prostate is included into a three-dimensional composite mechanical prostate image 92 in accordance with positioning in X,Y-plane as calculated in block 90 and Z-coordinate, which is considered proportional to the calculated in block 87 modified average for current frame 87. More detailed description of the three-dimensional image composition algorithm of this block is given below in the description for FIG. 10.

After prostate examination is complete, a procedure 97 of a final smoothing and three-dimensional interpolation is applied to current mechanical image 92. The final two-dimensional and three-dimensional mechanical prostate images are then prepared in block 98 representing a plurality of contour, slices, iso-surfaces and alike for a better visual perception. Such prostate parameters as prostate gland size (small/medium/large) 102, medium groove (absent/present) 103, prostate shape (symmetrical/asymmetrical) 104 are calculated directly from the final prostate image by testing these value to a predetermined acceptance criteria.

A nodule classifier includes three nodule detectors. First of them, shown in block 99, analyzes a signal distribution for prostate pressure data to detect specific features typical for a positive nodule presence. Second nodule detector, shown in block 100, applies a series of predetermined convolution filters to each two-dimensional prostate mechanical image to detect a nodule from a variety of possible nodule forms.

Preferably, a form of a convolution filter corresponds to what is being looked for in a nodule form. A third nodule detector, shown in block 101, applied a series of three-dimensional convolution filters to the final three-dimensional prostate image in block 98. Presence of specific three-dimensional objects inside a filtered prostate image signals a possible nodule presence and its location.

Figure 9:
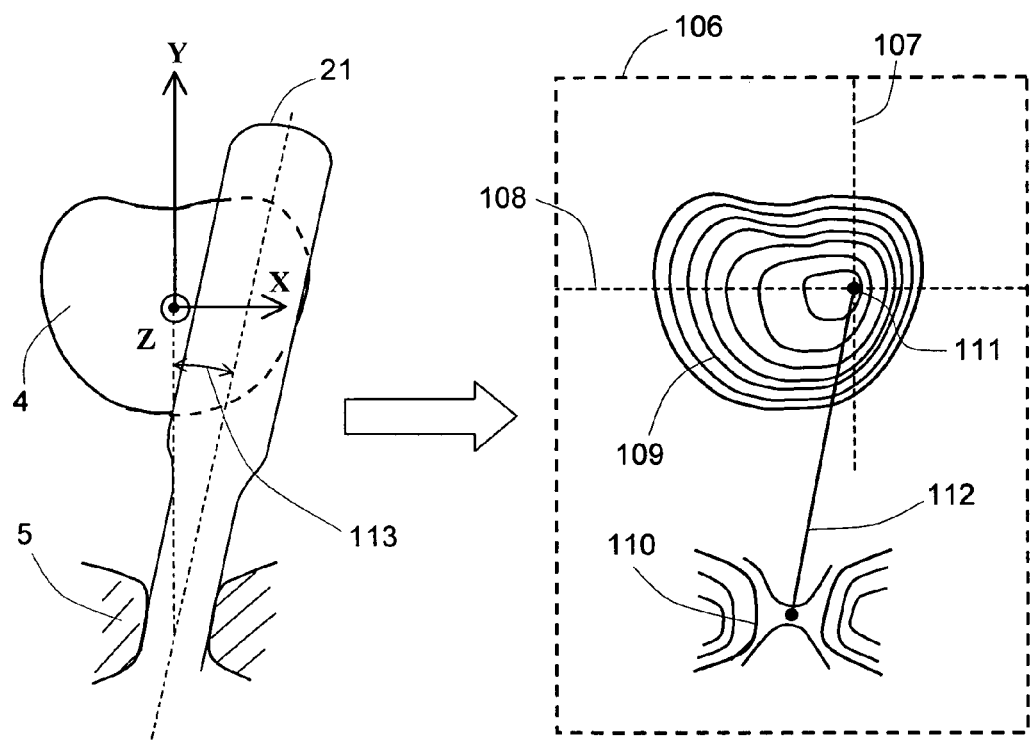
FIG. 9 is an illustration of real time two-dimensional prostate image and sphincter area mechanical image with relative probe positioning to guide the use of the probe during prostate examination.

FIG. 9 is an illustration of a sample real time two-dimensional prostate and sphincter area mechanical imaging with a relative probe positioning designed to guide the user during prostate examination. Multiple pressings of probe head 21 against the prostate 4 allow the head pressure sensor array to obtain pressure response data for the prostate. Each location when the probe is pressed against the prostate overlaps the previous such location. The pressure response data is then transformed into a composite two-dimensional mechanical prostate image 109 as described in FIG. 8 (block 91). At the same time, the shaft pressure sensor array provides supplemental mechanical data for the sphincter area, which is visualized in the same image frame 106 as a two-dimensional sphincter mechanical image 110. Using procedures in blocks 89, 90, and 93 described in FIG. 8, current coordinates 107, 108 of a probe head center 111 in the reference coordinate system X, Y, Z, as well as probe azimuth angle 113, and distance 112 between a sphincter center and the probe center 111 are then calculated. Combined visualization of the prostate image 109, the sphincter image 110 and the probe head position facilitates the prostate probe navigation and provides efficient feedback to the user.

Figure 10:
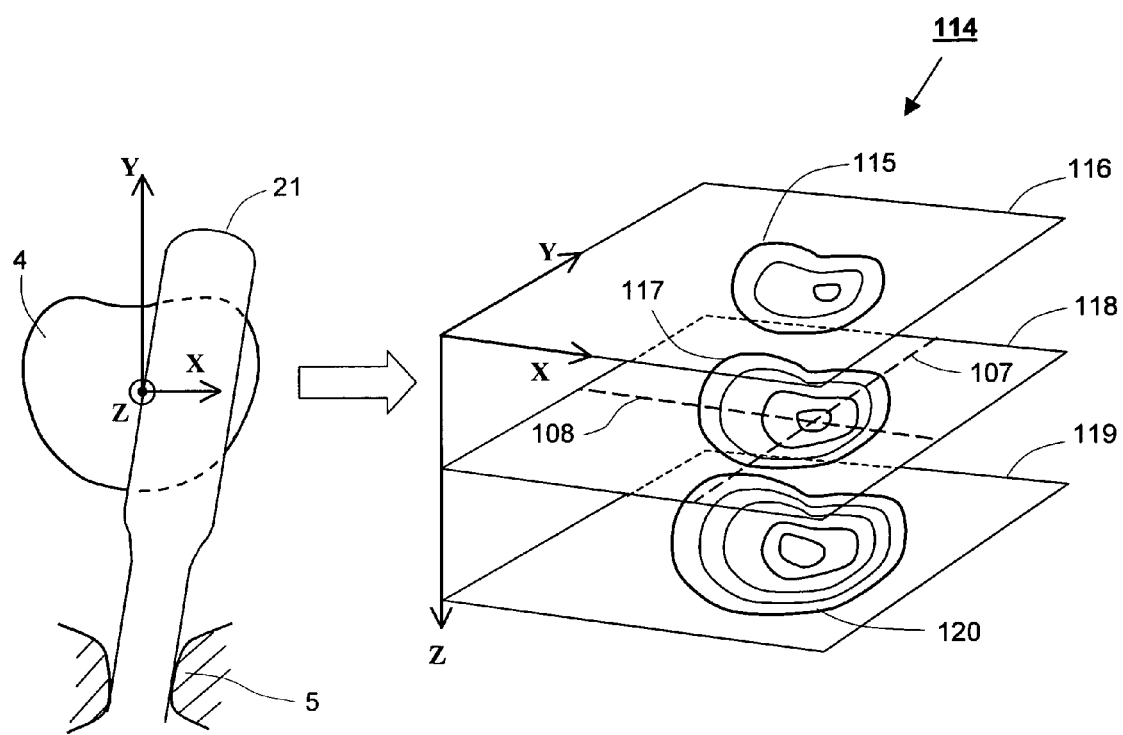
FIG. 10 is an illustration of a three-dimensional prostate mechanical image composition.

FIG. 10 is an illustration of a three-dimensional prostate mechanical image composition in accordance with the method of the present invention. The three-dimensional prostate mechanical image 114 (see also the description of block 92 in FIG. 8 above), includes a plurality of two-dimensional mechanical prostate images 115, 117, 120 placed inside planes 116, 118, 119 accordingly. During prostate scanning by multiple pressings of probe head 21 against the prostate 4, the head pressure sensor array provides pressure response data for the prostate. Each new portion of pressure response data is transformed into a two-dimensional partial mechanical prostate image in the accordance with procedure 85 and X, Y-frame coordinates for example 107, 108 as calculated by procedure 90 and Z-coordinate as calculated by procedure 87 from FIG. 8. Each pixel of this pressure response data is then placed inside a two-dimensional mechanical prostate image 117 with a predetermined weighted factor if its current pixel value exceeds a threshold value inside the two-dimensional prostate image 117. Preferably, two different three-dimensional mechanical prostate images are constructed: one image includes only normalized pressure response pixels (each pixel value of the prostate mechanical image is divided by a modified average of analyzed pressure response data frame), while another image includes only absolute pressure response pixels.

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method for mechanical stress pattern imaging of a palpable organ through a natural body opening comprising the steps of:

(a) providing a probe equipped with a two-dimensional pressure stress pattern sensor array adapted to obtain pressure stress pattern response data when pressed against said palpable organ, (b) conducting examination of said palpable organ by inserting said probe through said natural body opening and pressing said probe against said palpable organ at various locations about thereof to obtain said pressure stress pattern response data, each subsequent location overlapping a previous location, (c) obtaining a plurality of partial mechanical stress pattern images from said pressure response data from said pressure sensor, each subsequent and previous partial mechanical stress pattern image corresponding to the respective location of pressing of said probe against said palpable organ, (d) comparing each subsequent partial mechanical stress pattern image with the previous partial mechanical stress pattern image to find commonly identified features defining a two-dimensional overlap therebetween, and (e) constructing a composite mechanical stress pattern image of said palpable organ from said plurality of partial mechanical stress pattern images using said commonly identified features and overlaps between each subsequent and previous partial mechanical stress pattern image to merge them together, whereby the entire mechanical stress pattern image of said palpable organ is obtained with said two-dimensional pressure sensor array irrespective of the movements of said organ during examination.

2. The method as in claim 1, wherein said probe is further equipped with a supplemental pressure sensor array located in a known and fixed geometrical relationship to said pressure stress pattern sensor array along said probe, said step (b) further including obtaining supplemental pressure response data from said second pressure sensor array.

3. The method as in claim 2, wherein said step (b) further including identifying a preliminary position of said palpable organ at a predetermined distance from said supplemental reference organ as detected from said supplemental pressure response data.

4. A device for mechanical stress pattern imaging of a palpable organ through a natural body opening comprising:

a probe head sized to fit through said natural body opening, said probe head equipped with a two-dimensional head pressure sensor array adapted to obtain a pressure stress pattern response data when pressed against said palpable organ, an electronic unit connected to said probe head and adapted to receiving said pressure response data from said probe head, and a processing and display means connected to said electronic unit, said processing and display means further including a means for calculating a plurality of partial mechanical stress pattern images, each partial mechanical stress pattern image calculated from said pressure response data when said probe is pressed against said palpable organ, a means for comparing each subsequent partial stress pattern mechanical image with a previous partial stress pattern mechanical image to find commonly identified features so as to determine a two-dimensional overlap therebetween, and a means for constructing a composite image of said palpable organ from said plurality of partial images by merging them together using said overlap.

5. The probe as in claim 4, wherein said probe head pressure sensor array includes a plurality of individual pressure stress pattern sensors, each said stress pattern sensor selected from a group consisting of capacitive pressure transducer, piezoelectric pressure transducer, resistive pressure transducer, and MEMS pressure transducer.

6. The probe as in claim 5, wherein the number of said individual sensors in said plurality exceeds 60.

7. The probe as in claim 4, wherein said probe head further includes a shaft equipped with a shaft pressure sensor array spaced away from the head pressure sensor array and adapted to obtain a supplemental pressure response data.

* * * * *